(12) United States Patent
Roszell (10) Patent No.: US 11,439,602 B2
(45) Date of Patent: Sep. 13, 2022

(54) COMPOSITION AND METHOD FOR TRANSDERMAL DELIVERY OF CANNABIDIOL (CBD) AND Δ⁹-TETRAHYDROCANNABINOL (THC)

(71) Applicant: Ovation Science Inc., Vancouver (CA)

(72) Inventor: James A. Roszell, Las Vegas, NV (US)

(73) Assignee: Ovation Science Inc., Vancouver (CA)

( * ) Notice: Subject to any disclaimer, the term of this patent is extended or adjusted under 35 U.S.C. 154(b) by 0 days.

(21) Appl. No.: 17/170,231

(22) Filed: Feb. 8, 2021

(65) Prior Publication Data

US 2021/0251912 A1 Aug. 19, 2021

Related U.S. Application Data

(60) Provisional application No. 62/978,034, filed on Feb. 18, 2020.

(51) Int. Cl.
*A61K 9/70* (2006.01)
*A61K 31/352* (2006.01)
*A61K 31/05* (2006.01)

(52) U.S. Cl.
CPC ............ *A61K 9/7053* (2013.01); *A61K 31/05* (2013.01); *A61K 31/352* (2013.01)

(58) Field of Classification Search
None
See application file for complete search history.

(56) References Cited

U.S. PATENT DOCUMENTS

| | | |
|---|---|---|
| 3,817,887 A | 6/1974 | Mestetsky |
| 4,035,506 A | 7/1977 | Lucas et al. |
| 4,301,145 A | 11/1981 | Cestari |
| 4,384,903 A | 5/1983 | Enever |
| 4,440,741 A | 4/1984 | Marschner |
| 4,448,906 A | 5/1984 | Deinet et al. |
| 4,500,338 A | 2/1985 | Young et al. |
| 4,507,279 A | 3/1985 | Okuyama et al. |
| 4,645,794 A | 2/1987 | Davis et al. |
| 4,671,957 A | 6/1987 | Holtshousen |
| 4,803,066 A | 2/1989 | Edwards |
| 4,810,489 A | 3/1989 | Murray et al. |
| 4,840,687 A | 6/1989 | Forsberg et al. |
| 4,897,259 A | 1/1990 | Murray et al. |
| 4,971,800 A | 11/1990 | Chess et al. |
| 5,019,604 A | 5/1991 | Lemole |
| 5,045,317 A | 9/1991 | Chess et al. |
| 5,051,260 A | 9/1991 | Chess et al. |
| 5,055,303 A | 10/1991 | Riley, Jr. |
| 5,082,656 A | 1/1992 | Hui et al. |
| 5,126,136 A | 6/1992 | Merat et al. |
| 5,155,199 A | 10/1992 | Hayashi |
| 5,232,691 A | 8/1993 | Lemole |
| 5,266,329 A | 11/1993 | Riley, Jr. |
| 5,298,534 A | 3/1994 | Prosise et al. |
| 5,320,838 A | 6/1994 | Woller |
| 5,336,305 A | 8/1994 | Staats |
| 5,370,876 A | 12/1994 | Noll et al. |
| 5,389,363 A | 2/1995 | Snyder et al. |

(Continued)

FOREIGN PATENT DOCUMENTS

| | | |
|---|---|---|
| DE | 195 43 989 A1 | 5/1997 |
| EP | 0 260 030 A2 | 3/1988 |

(Continued)

OTHER PUBLICATIONS

Bradley, C. et al., "Noninvasive Transdermal Chemical Collection", Skin Pharmacol, vol. 3, pp. 218-226 (1990).
Hasirci, V., "Synthesis and characterization of PVNO and PVNO-PVP hydrogels", Biomaterials, vol. 2, No. 1, 7 pages (Jan. 1981).
Material Safety Data Sheet, Gantrez S-97 BF Solution, ISP Technologies, Inc., 6 pages (Apr. 7, 1994).
Material Safety Data Sheet, Ganex V-216, ISP Technologies, Inc., pp. 5 pages (Sep. 16, 1994).
Material Safety Data Sheet, Ganex V-220, ISP Technologies, Inc., 5 pages (Oct. 7, 1998).
Nair, P. et al., "Studies on the effect of degree of hydrophilicity on tissue response of polyurethane interpenetrating polymer networks", Biomaterials, vol. 13, No. 8, pp. 537-542 (1992).

(Continued)

*Primary Examiner* — Jessica Worsham
(74) *Attorney, Agent, or Firm* — Merchant & Gould P.C.

(57) ABSTRACT

A transdermal delivery composition for the delivery to skin and the penetration of the skin includes: (a) a therapeutic effective amount of a cannabinoid mixture, wherein the cannabinoid mixture comprises cannabidiol (CBD) and Δ⁹-tetrahydrocannabinol (THC) at a weight ratio of about 1:20 to about 20:1; (b) a hydrophilic polymer/hydrophobic polymer adduct in an amount sufficient to hold the cannabinoid composition and provide a sustain release of the cannabinoid mixture after application to skin tissue over a time period of at least 6 hours; (c) a penetrant component in an amount sufficient to assist with a transdermal penetration of the cannabinoid mixture through skin tissue once the composition has been applied to skin tissue; (d) a surfactant component in an amount sufficient to stabilize the polymer adduct and release the cannabinoid mixture from the transdermal delivery composition upon application to skin tissue; and (e) at least about 70 wt. % water. A method of application of a transdermal delivery composition to skin tissue includes applying the transdermal delivery composition to skin tissue and spreading the composition to form a film on the skin tissue. A method for formulating a transdermal delivery composition based on a desired penetration weight ratio of CBD to THC through skin tissue includes selecting a formulation weight ratio of CBD to THC for formulating the composition, wherein the weight ratio is determined by multiplying the desired penetration weight ratio of CBD to THC by a CBD/TCH delivery factor, wherein the CBD/THC delivery factor.

10 Claims, 7 Drawing Sheets

(56) References Cited

U.S. PATENT DOCUMENTS

| | | | |
|---|---|---|---|
| 5,417,968 A | 5/1995 | Staats | |
| 5,431,756 A | 6/1995 | Kosowski et al. | |
| 5,508,024 A | 4/1996 | Tranner | |
| 5,597,849 A | 1/1997 | McGinity et al. | |
| 5,605,676 A | 2/1997 | Gaffar et al. | |
| 5,607,979 A | 3/1997 | McCreery | |
| 5,618,850 A | 4/1997 | Coury et al. | |
| 5,622,993 A | 4/1997 | McGinity et al. | |
| 5,658,559 A | 8/1997 | Smith | |
| 5,674,912 A | 10/1997 | Martin | |
| 5,707,612 A | 1/1998 | Zofchak et al. | |
| 5,721,306 A | 2/1998 | Tsipursky et al. | |
| 5,725,844 A | 3/1998 | Gers-Barlag et al. | |
| 5,725,875 A | 3/1998 | Noll et al. | |
| 5,730,966 A | 3/1998 | Torgerson et al. | |
| 5,736,128 A | 4/1998 | Chaudhuri et al. | |
| 5,747,022 A | 5/1998 | Slavtcheff | |
| 5,807,957 A | 9/1998 | Samour et al. | |
| 5,834,538 A | 11/1998 | deHullu et al. | |
| 5,869,593 A | 2/1999 | Helmeke et al. | |
| 5,874,074 A | 2/1999 | Smith | |
| 5,891,470 A | 4/1999 | Rinaldi et al. | |
| 5,906,822 A | 5/1999 | Samour et al. | |
| 5,911,980 A | 6/1999 | Samour et al. | |
| 5,939,453 A | 8/1999 | Heller et al. | |
| 5,942,545 A | 8/1999 | Samour et al. | |
| 5,955,109 A | 9/1999 | Won et al. | |
| 5,968,543 A | 10/1999 | Heller et al. | |
| 5,968,919 A | 10/1999 | Samour et al. | |
| 5,976,566 A | 11/1999 | Samour et al. | |
| 5,980,876 A | 11/1999 | Peffly | |
| 6,074,527 A | 6/2000 | Hsu et al. | |
| 6,096,344 A | 8/2000 | Liu et al. | |
| 6,177,068 B1 | 1/2001 | Shih et al. | |
| 6,183,766 B1 | 2/2001 | Sine et al. | |
| 6,190,689 B1 | 2/2001 | Hoffmann et al. | |
| 6,255,421 B1 | 7/2001 | Plochocka et al. | |
| 6,294,186 B1 | 9/2001 | Beerse et al. | |
| 6,582,683 B2 | 6/2003 | Jezior | |
| 6,583,220 B1 | 6/2003 | Lipman | |
| 6,627,217 B1 | 9/2003 | Suzuki et al. | |
| 6,630,507 B1 | 10/2003 | Hampson et al. | |
| 6,756,059 B2 | 6/2004 | Roszell et al. | |
| 6,881,400 B2 | 4/2005 | Collin | |
| 7,674,471 B2 | 3/2010 | Roszell et al. | |
| 8,128,913 B1 | 3/2012 | Roszell et al. | |
| 8,293,786 B2 * | 10/2012 | Stinchcomb | A61P 17/14 514/483 |
| 8,318,818 B2 | 11/2012 | Roszell et al. | |
| 8,481,058 B2 | 7/2013 | Jezior | |
| 9,763,991 B2 | 9/2017 | Bray et al. | |
| 2002/0051797 A1 | 5/2002 | Jezior | |
| 2003/0044374 A1 | 3/2003 | Roszell et al. | |
| 2004/0126339 A1 | 7/2004 | Roszell | |
| 2005/0089491 A1 | 4/2005 | Collin | |
| 2005/0118214 A1 | 6/2005 | Najdek et al. | |
| 2005/0175571 A1 | 8/2005 | Roszell et al. | |
| 2010/0173904 A1 | 7/2010 | Roszell et al. | |
| 2015/0126595 A1* | 5/2015 | Smith | A61K 31/01 514/454 |

FOREIGN PATENT DOCUMENTS

| | | |
|---|---|---|
| EP | 0 391 741 A2 | 10/1990 |
| EP | 0 640 352 A1 | 3/1995 |
| EP | 0 747 062 A2 | 12/1996 |
| EP | 0 945 120 A1 | 9/1999 |
| JP | 7-89826 A | 4/1995 |
| JP | 10-67618 A | 3/1998 |
| JP | 10-95714 A | 4/1998 |
| JP | 2002-104920 A | 4/2002 |
| WO | WO 93/24105 A1 | 12/1993 |
| WO | WO 94/23693 A1 | 10/1994 |
| WO | WO 01/17488 A1 | 3/2001 |
| WO | WO 03/015821 A1 | 2/2003 |

OTHER PUBLICATIONS

Shinichi, N. et al., "Hair treatment agent—includes specific high molecular copolymer compounds by which skin layer is made to form on hair surface", Derwent Abstract (ACC#1998-280363; Week# 199825) (1999).

Tiller et al., "Designing surfaces that kill bacteria on contact," http://www/pnas.org/cgi/content/abstract/98/11/5981, PNAS Online, 2 pages (May 22, 2001).

Declaration of James A. Rozell dated Apr. 2, 2009 (with attachments).

Japanese Office Action dated Feb. 7, 2008 from corresponding Japanese patent Application No. 2003-520779.

Canadian Office Action dated Aug. 12, 2009 from corresponding Canadian Application No. 2,457,124.

Australian Office Action dated Aug. 11, 2006 from corresponding Australian Application No. 2002355964.

International Search Report dated Dec. 6, 2002 for corresponding PCT Application No. PCT/US02/26301.

Written Opinion dated Jan. 9, 2004 for corresponding PCT Application No. PCT/US02/26301.

Supplementary European Search Report for Application No. 02752847.0 dated Nov. 5, 2009.

Complaint for Patent, Trademark Infringement and Misappropriation of Trade Secrets with Exhibits 1-5, *Skinvisible Pharmaceuticals, Inc. v. Sunless Beauty, Ltd.* Case No. 2:11-CV-1591 JCM-CWH. District Court of Nevada, dated Sep. 30, 2011.

Disclosure of Asserted Claims and Infringement Contentions with Exhibits 1-8, *Skinvisible Pharmaceuticals, Inc. v. Sunless Beauty, Ltd.* Case No. 2:11-CV-1591 JCM-CWH. District Court of Nevada, dated Dec. 15, 2011.

Application for Default Judgment Against Defendants *TMTA, LLC d/b/a Solerra, Angie Trelstad*, Individually, Angie Trelstad as Member/ Manager of TMTA, LLC and Angie Trelstad as President of Sunless Beauty, Ltd., *Skinvisible Pharmaceuticals, Inc. v. Sunless Beauty, Ltd.* Case No. 2:11-CV-1591 JCM-CWH. District Court of Nevada, dated Feb. 13, 2012.

Davis, RH et al.; "Processed Aloe vera administered topically inhibits inflammation," Journal of American Podiatric Association, vol. 79, No. 8, pp. 395-397; published Aug. 1989, abstract only provided.

Davis, RH; "Aloe vera as a biologically active vehicle for hydrocortisone acetate," Journal of American Podiatric Association, vol. 81, No. 1, pp. 1-9; abstract only provided.

Merriam Webster's Collegiate Dictionary, Tenth Edition, 1996, Merriam-Webster Inc. p. 311.

Goddard, E. Desmond; Gruber, James V.; Principles of Polymer Science and Technology in Cosmetics and Personal Care, 1999; Marcel Dekker Inc; (see Entry for PVP/Eicosene copolymer & PVP/Hexadecane), pp. 3,4.

Product Literature for Ganex V-200™, Ganex V-216™ and Ganex WP 660 (downloaded from http.//online1.ispcorp.com on Sep. 29, 2008.

Merck Index entries for "Aloe", "Hydrocortisone", and "Salicylic Acid" as retrieved from Knovel on Jun. 6, 2013, pp. 1-9 as provided.

Hayat et al. "Salicylic Acid: A Plant Hormone", 2007, SPRINGER, Chapter 1, pp. 1-14.

"A Dictionary of Science" 6th ed., OXFORD University Press, 2010, enty for "cortisol", p. 198.

Strickland et al.; "Industrial processing and quality control of Aloe barbadensis (*Aloe vera*) gel", 2004, CRC Press, pp. 1-68 as provided.

Sigma Aldrich product information for "Poly(4-vinylpyridine)" and "Poly(vinylpolypyrrolidone)", as retrieved from <www.sigmaaldrich. com> on Jun. 5, 2013, pp. 1-2 as provided.

Sweetman, Sean C.; "Martindale: The Complete Drug Reference",33rd ed., 2002, Pharmaceutical Press,§ "Corticosteroids", pp. 1490-1546.

(56) References Cited

OTHER PUBLICATIONS

Dictionary.com entries for the terms:"drug", "steroidal", and "anti-inflammatory", pp. 1-8, as provided.
Cannabinoids—What is Medical Marijuana, http://mychronicrelief.com/cannabis-science/cannabinoids/, 8 pages.
Dr. Malik Burnett, "Finding the Optimal Therapeutic Ratio of THC and CBD," https://www.medicaljane.com/2014/05/29/finding-the-optimaltherapeutic-ratio-of-thc-and-cbd/, 3 pages (May 29, 2014).
Naef et al., "The analgesic effect of oral delta-9-tetrahydrocannabinol (THC), morphine, and a THC-morphine combination in healthy subjects under experimental pain conditions," Pain, vol. 105, pp. 79-88 (2003).
Parker et al., "Regulation of nausea and vomiting by cannabinoids," British Journal of Pharmacology, vol. 163, pp. 1411-1422 (2011).

* cited by examiner

COMPOSITION AND METHOD FOR TRANSDERMAL DELIVERY OF CANNABIDIOL (CBD) AND Δ⁹-TETRAHYDROCANNABINOL (THC)

This application claims priority to U.S. Application Ser. No. 62/978,034 that was filed with the United States Patent and Trademark Office on Feb. 18, 2020. The entire disclosure of U.S. Application Ser. No. 62/978,034 is incorporated herein by reference.

BACKGROUND

In many countries, growth and use of *Cannabis* plants is restricted due to the presence of the psychoactive compound tetrahydrocannabinol (THC), along with other cannabinoid compounds that do not necessarily share THC's psychoactive effects.

Some medical uses of *Cannabis* extracts and isolated compounds are recognized in published peer reviewed literature, and continue to stimulate increased interest among physicians and patients for multiple medical applications. For instance, *cannabis* extracts are included in a SATIVEX product approved by regulatory authorities in UK, Spain, New Zealand, and Canada to treat spasticity in multiple sclerosis (http://www.gwpharm.com/Sativex.aspx).

U.S. Pat. No. 6,630,507 to Hampson et al. describes *Cannabis* spp. isolated compounds called cannabinoids that have antioxidant La properties, and mentions possible use in the treatment of ischemic, age-related, inflammatory, and autoimmune diseases. The cannabinoids are said to have particular applications as neuroprotectants, for example in limiting neurological damage following ischemic insults, such as stroke and trauma, or in the treatment of neurodegenerative diseases, such as Alzheimer's disease, Parkinson's disease, and HIV related dementia. Cannabidiol is mentioned in particular, as it lacks the toxic and psychoactive effects of THC.

U.S. Pat. No. 9,763,991 to Bray et al. describes use of cannabinol for treatment of various neurobehavioral disorders, sleep deprivation, anxiety disorders, and post-traumatic stress disorder. The patent describes delivery of the cannabinol via an oral composition.

Cannabidiol (CBD) and tetrahydrocannabinol (THC) are known cannabinoid compounds that exist in the human body and have a regulatory role. Endocannabinoids are produced in the human body and contribute to governing the physiological processes of pain modulation, immune function, newborn suckling, appetite reward, thermoregulation, memory, and inflammation regulation.

Smoking *Cannabis*, has been known to decrease nausea and vomiting associated with cancer chemotherapy since the late 1970's (Parker et al., British Journal of Pharmacology (2011) 163 1411-1422). The major component of most *cannabis* strains is □⁹-Tetrahydrocannabinol (THC). THC is responsible for the "high" associated with *cannabis* use. In addition to THC's anti-emetic use, it is also anti-inflammatory and analgesic. Indeed, given in oral doses of 15-20 mg, THC (Naef et al., Pain 105 (2003) 79-88) decreased cancer pain comparable to 120 mg of codeine. What would seem to be a wonderful drug for nausea, inflammation and pain, has the drawbacks of causing paranoia, anxiety, tachycardia, and THC's high.

The second most common cannabinoid found in the *cannabis* plant is Cannabidiol (CBD). CBD has many beneficial therapeutic effects of its own, sharing those of THC, and additionally, CBD also has anti-anxiety, anti-seizure, and anti-psychotic effects (Marijuanadoctors.com; CBD: THC ratios). CBD has also been shown to moderate the high associated with THC.

It appears that CBD and THC together have a greater therapeutic effect than either one alone (http://mychronicrelief.com/*cannabis*-science/cannabinoids/). Many ratios of CBD to THC, 0:1 to 40:1, have been proposed for a variety of uses and treatments. CBD-rich products are marketed toward those seeking relief from anxiety, arthritis, seizures, stress, inflammation, and overall wellness, not necessarily a high. Therefore, several different ratios of CBD:THC are desirable to deliver specific types of therapeutic experiences.

Alternative delivery systems for CBD and THC to the human body are desired, such as through the skin. Such a delivery can be referred to as a transdermal delivery. A number of issues need to be addressed to effect a transdermal delivery of CBD and THC. One issue is providing a sustained and controlled release of the CBD and THC to skin tissue over time. A composition that releases all or almost all of its CBD and THC at once may result in CBD and THC being wiped away or washed away before it can be taken systemically through the skin, and would have to be frequently applied. A composition that holds onto its CBD and THC may not allow the CBD and THC to be available for transdermal delivery. In addition, it may be desirable for the CBD and THC to be available for transdermal delivery over a period of time. Another issue is that human skin generally functions to resist a transdermal delivery of many actives. Accordingly, a composition of pure CBD and THC may not effectively penetrate skin tissue for systemic effect. Furthermore, providing a desired penetration weight ratio of CBD to THC through skin tissue from a transdermal delivery system is not as simple as mixing the CBD and THC into a composition at that weight ratio. The release ratio of the CBD and THC from the composition and the subsequent penetration ratio of the CBD and THC through the skin can alter the ultimate ratio of CBD and THC that is administered or finally delivered.

Compositions are available for the transdermal delivery of certain active components. Exemplary compositions are described in, for example, U.S. Pat. Nos. 8,481,058 and 8,318,818, both assigned to Skinvisible Pharmaceuticals, Inc.

SUMMARY

A transdermal delivery composition for the delivery to skin and the penetration of the skin is provided by the present disclosure. The transdermal delivery composition includes: (a) a therapeutic effective amount of a cannabinoid mixture, wherein the cannabinoid mixture comprises cannabidiol (CBD) and Δ⁹-tetrahydrocannabinol (THC) at a weight ratio of about 1:20 to about 20:1; (b) a hydrophilic polymer/hydrophobic polymer adduct in an amount sufficient to hold the cannabinoid composition and provide a sustain release of the cannabinoid mixture after application to skin tissue over a time period of at least 6 hours; (c) a penetrant component in an amount sufficient to assist with a transdermal penetration of the cannabinoid mixture through skin tissue once the composition has been applied to skin tissue; (d) a surfactant component in an amount sufficient to stabilize the polymer adduct and release the cannabinoid mixture from the transdermal delivery composition upon application to skin tissue; and (e) at least about 70 wt. % water.

A method of application of a transdermal delivery composition to skin tissue is provided by the present disclosure.

The method includes applying the transdermal delivery composition to skin tissue and spreading the composition to form a film on the skin tissue. The transdermal delivery composition can generally be noticed within about 15 to 20 minutes, and can be re-applied as desired.

A method for formulating a transdermal delivery composition based on a desired penetration weight ratio of CBD to THC through skin tissue is provided by the present disclosure. The method includes selecting a formulation weight ratio of CBD to THC for formulating the composition, wherein the weight ratio is determined by multiplying the desired penetration weight ratio of CBD to THC by a CBD/TCH delivery factor, wherein the CBD/THC delivery factor.

DETAILED DESCRIPTION

A composition for transdermal delivery of cannabidiol (CBD) and $\Delta^9$-tetrahydrocannabinol (THC) can be referred to as a transdermal delivery composition or more conveniently to as a delivery composition. The actives of the composition are CBD and THC and can be referred to as cannabinoids.

The purpose of the transdermal delivery composition is to deliver both CBD and THC to skin tissue over time, and then permit the CBD and THC to be taken systemically through the skin tissue. As a result, the transdermal delivery composition is provided so that it holds onto both the CBD and THC while also releasing the CBD and THC over a time period of about 4 to 12 hours, and preferably about 4 to 6 hours. During this time period, the release can be considered relatively consistent and sustained. This release can also be referred to as a prolonged release since a majority of the CBD and THC is not released within the first half hour. In addition to the prolonged and sustained release of CBD and THC, the transdermal delivery composition enhances the transmission of the CBD and THC through the skin tissue compared to a composition of pure CBD and THC. Accordingly, the transdermal delivery composition provides for both sustained and prolonged release, and also enhanced transmission or uptake through the skin tissue.

The transdermal delivery composition can include a polymer adduct which can be considered a hydrophilic polymer/hydrophobic polymer adduct that holds onto the cannabinoids and provides a desired release of the cannabinoids over time. In addition, the transdermal delivery composition includes surfactants for helping solubilize the hydrophobic polymers/hydrophilic polymer adduct and for assisting in the release of the cannabinoids from the polymer adduct. In addition, the transdermal delivery composition can include a penetrant component to assist with the penetration of the cannabinoids through the skin tissue. The transdermal delivery composition can additionally include emollients, chelating agents, antioxidants, preservatives, and a pH neutralizer.

The transdermal delivery composition can be summarized Table 1 below.

TABLE 1

Transdermal Delivery Composition

| Component | Amount (wt. %) |
| --- | --- |
| Water | 70-90, preferred 75-85 |
| Polymer adduct | 4-9, preferred 4.5-8, more preferred 5-6 |
| Surfactants | 3-9, preferred 3.5-8, more preferred 4-6 |
| Penetrants | 2-10, preferred 3-7, more preferred 3.5-5 |
| Cannabinoids | 0.05-2, preferred 0.1-1.5 |
| Antioxidants | Optional but if present, present in a range of 0.1-1, preferred 0.2-0.5 |
| Chelating agent | Optional but if present, present in a range of 0.01-0.1 |
| Preservative | Optional but if present, present in a range of 0.1-2, preferably 0.5-1.5 |
| Emollient | Optional but if present, present in a range of 1-5, preferably 1.5-4 |
| pH neutralizing agent | Amount affective to provide a pH of 6-7.5 |

Cannabinoids

The transdermal delivery composition can deliver a desired or target weight ratio of cannabidiol (CBD) and $\Delta^9$-tetrahydrocannabinol (THC) through skin tissue. A target weight ratio of CBD and THC can provide benefits systemically. While the target weight ratio can be a 1:1 weight ratio, alternative weight ratios are found to be more desired. An exemplary weight ratio of CBD to THC can be a weight ratio of about 1:20 to about 20:1. Alternative weight ratios of CBD to THC include about 1:15 to about 15:1, about 1:10 to about 10:1, about 1:5 to about 5:1, and about 1:3 to about 3:1.

Both cannabidiol and $\Delta^9$-tetrahydrocannabinol have similar structures. The structures of cannabidiol and of $\Delta^9$-tetrahydrocannabinol are provided below:

$\Delta^9$-tetrahydrocannabinol (CBD)

cannabidiol

The transdermal delivery composition can include an amount of the cannabinoids to provide a desired effect. Furthermore, because of the effectiveness of the transdermal delivery composition in both releasing the cannabinoids and in facilitating the transdermal delivery or uptake of cannabinoids through skin tissue, an amount of the cannabinoids in the transdermal delivery composition can be provided at a level that is less than would be expected to achieve the same effect. The amount of cannabinoids (combination of CBD and THC) in the transdermal delivery composition can be about 0.05 wt. % to about 2 wt. %, and can preferably be about 0.1 wt. % to about 1.5 wt. %. A particular advantage of the transdermal delivery composition is the ability to utilize a relatively small amount of the cannabinoids and effectively deliver it through the skin tissue thereby avoiding the cost associated with other compositions using substantially more of the cannabinoids to obtain a similar effect.

CBD and THC are sparingly soluble in aqueous buffers, but they are readily soluble in organic solvents. Using an organic solvent, however, complicates the delivery process through skin tissue since skin tissue generally poorly tolerates organic solvents. By using a hydrophobic polymer delivery system containing, for example, an abundance of polyvinylpyrrolidone polymers with C16, C20, and in some cases C30 side chains, the CBD and THC can be readily soluble therein. Because the CBD and THC bind so tightly in such a hydrophobic polymer system, it is difficult to release the CBD and THC therefrom unless steps are taken.

In general, a transdermal delivery process of delivering a topical product through skin tissue involves a two-step process. First, the active ingredient(s) are released from the vehicle, in this case the polymers. Active ingredient(s) that are not released will have no therapeutic effect. Second, the active ingredient(s) penetrate the skin tissue, an organ whose nature is to prevent this process.

Active ingredient released from a hydrophobic polymer system can be facilitated in at least two ways. The first is by addition of surfactants that will help the release thereof. By choosing certain surfactants, an increases in the partition of the active ingredient(s) from the polymer system can be enhanced when the polymer system includes a hydrophobic phase and a aqueous phase, thus enhancing the release of the active(s). The second method is to decrease the hydrophobic character of the polymer composition. The polymer compositions described herein are capable of adjustment to favor a lower level of hydrophobic character.

Once the active ingredient(s) are released from the polymer delivery system, the active ingredient(s) need to penetrate the skin tissue. An issue regarding penetration of the skin tissue is the molecular weight of the active ingredient(s). A molecular weight of less than 600 to 1000 is generally regarded as having the best chance of penetrating the skin tissue. CBD and THC both have a molecular weight of 314.22, well below the exclusion limit of the skin. It is helpful that the active ingredient(s) have no charge and are slightly hydrophobic. There are a large number of compounds that are known as skin penetrants, and they can be used to advantage.

Polymer Adduct

The polymer adduct can be prepared according to U.S. Pat. Nos. 8,318,818 and 8,481,058, the disclosures of which are incorporated herein by reference. The polymer adduct can be prepared by melt processing a hydrophobic polymer composition and a hydrophilic polymer composition to provide an interaction between the hydrophobic polymer composition and the hydrophilic polymer composition. It should be understood that the phrase "melt processing" refers to mixing the hydrophobic polymer composition and the hydrophilic polymer composition under conditions that provide that the hydrophobic polymer component of the hydrophobic polymer composition and the hydrophilic polymer component of the hydrophilic polymer composition are in a liquid state so that they sufficiently mix. When the polymers are sufficiently mixed, an interaction forms between the hydrophobic polymer component and the hydrophilic polymer component. The melt processing temperature is preferably at least about 90° C., more preferably at least about 100° C., and more preferably at least about 105° C. to generate this interaction.

The interaction exhibited between the hydrophobic polymer component and the hydrophilic polymer component can be considered a type of complex formation reaction, and that the complexes, once formed, are stable in water at temperatures up to 65° C. and at a pH range of 3.0 to 9.0. By stable, it is meant that the complexes do not favor disassociation. This interaction provides the composition with an ability to bind or hold onto the cannabinoids that are emulsified in water, and provides the composition with an ability to bind to skin and/or substrates of predominantly hydrophobic character.

Hydrophobic Polymer Composition

The hydrophobic polymer composition that can be used includes repeating pyrrolidone/alkylene groups. Exemplary polymers that have repeating pyrrolidone/alkylene groups include those polymers obtained by a polymerizing alkylene substituted vinylpyrrolidone. The polymers can be represented by the following general formula:

wherein R represents a carbon chain substitute such as an alkylene group and n represents the number of repeating units. The R group is preferably sufficiently long so that the polymer remains relatively water insoluble and should not be too long so that the polymer is difficult to melt process. Preferably, the alkylene group contains a length of at least about 10 carbon atoms and contains no more than about 25 carbon atoms. Preferably, the alkylene group contains between about 14 carbon atoms and about 22 carbon atoms, and more preferably between about 15 carbon atoms and about 19 carbon atoms.

The poly(vinylpyrrolidone/alkylene) polymers that can be used preferably have a molecular weight that is sufficiently high so that the polymer maintains its water insolubility but the molecular weight should not be so high that it becomes difficult to melt process the polymer. Preferably, the weight average molecular weight of the poly(vinylpyrrolidone/alkylene) polymer is between about 3,000 and about 400,000. Another way to characterize the size of the poly(vinylpyrrolidone/alkylene) polymer is by the number of repeating units (n). In the case of a poly(vinylpyrrolidone/alkylene) polymer having a weight average molecular weight of between about 6,000 and about 30,000, the poly(vinylpyrrolidone/alkylene) polymer has between about 20 and about 80 repeating units, and more preferably between about 30 and about 50 repeating units. It should be understood that repeating units refer to the residues of vinylpyrrolidone/alkylene groups.

Preferred poly(vinylpyrrolidone/alkylene) polymers that can be used include poly(vinylpyrrolidone/1-eicosene) and poly(vinylpyrrolidone/hexadecene). Poly(vinylpyrrolidone/1-eicosene) can be referred to as PVPE and is commonly used in pharmaceutical and cosmetic preparations. A preferred form of PVPE for use according to the invention includes about 43 to 44 repeating units in length and has a weight average molecular weight of about 17,000 and can be characterized as a paraffin-like solid. This particular PVPE is highly insoluble in water, and has an extremely low oral toxicity ($LD_{50}$>17000 mg/kg) and exhibits no demonstrable dermal toxicity. Poly(vinylpyrrolidone/1-hexadecene) can be referred to as PVPH. A preferred form of PVPH is available as a viscous yellow liquid that is insoluble in water and has a low oral toxicity ($LD_{50}$>64000 mg/kg), has about 39 to 40 repeating units, a molecular weight of about 12,000, and exhibits no demonstrable dermal toxicity.

PVPE and PVPH differ in the length of the hydrocarbon side chain, and are used extensively in the skin care industry, usually in concentrations of less than 1% by weight, because of their ability to bind to skin. Because the skin care industry generally prefers to apply actives to skin using a water-based composition, the use of PVPE and PVPH often requires solvents, surfactants, and emulsifiers to stabilize these polymers in a water emulsion. However, many of the solvents, surfactants and emulsifiers used to stabilize PVPE and PVPH in a water emulsion lack the low dermal toxicities of PVPE and PVPH. PVPE and PVPH by themselves lack a cosmetically elegant appeal when applied directly to the skin. They tend to be sticky and greasy.

The hydrophobic polymer composition is preferably provided as a mixture of different poly(vinylpyrrolidone/alkylene) polymers. The mixtures of different poly(vinylpyrrolidone/alkylene) polymers preferably include at least 5 wt. % of a first poly(vinylpyrrolidone/alkylene) polymer based on the weight of the hydrophobic polymer composition. The hydrophobic polymer composition preferably includes between about 5 wt. % and about 54 wt. % of the first poly(vinylpyrrolidone/alkylene) polymer. The second poly(vinylpyrrolidone/alkylene) polymer is preferably provided in an amount of at least about 46 wt. % and preferably in a range of between about 46 wt. % and 95 wt. %. For a hydrophobic polymer composition containing a first poly(vinylpyrrolidone/alkylene) polymer and a second poly(vinylpyrrolidone/alkylene) polymer, the mole ratio of the first polymer to the second polymer is preferably between about 1:22 and about 1:1. In general, when the hydrophobic polymer composition contains a mixture of different poly(vinylpyrrolidone/alkylene) polymers, it is preferable to provide at least one of the poly(vinylpyrrolidone/alkylene) polymers in an amount that provides improved properties to the composition compared to a composition having a hydrophobic polymer composition containing a single poly(vinylpyrrolidone/alkylene) polymer.

When the hydrophobic polymer composition is provided as a mixture of PVPH and PVPE, it is preferable that the PVPH is provided in the range of between about 46 wt. % to about 95 wt. % and the PVPE is provided in the range of between about 5 wt. % and about 65 wt. %, based upon the weight of the hydrophobic polymer composition.

Hydrophilic Polymer Composition

The hydrophilic polymer composition that can be used includes at least one hydrophilic polymer and may include a mixture of hydrophilic polymers. The hydrophilic polymers that can be used include polymers having repeating carboxylic acid groups and/or hydroxyl groups. Preferred hydrophilic polymers that can be used according to the invention include polyacrylic acid polymers and poly(maleic acid/methylvinylether) copolymers.

Polyacrylic acid polymers that can be used preferably have a weight average molecular weight of at least about 50,000, and more preferably between about 50,000 and about 4,000,000. In addition, the polyacrylic acid polymers preferably have a level of cross-linking that is less than about 1%. A general structural representation of polyacrylic acid polymers is shown below:

wherein n is the number of repeating units and is preferably between about 1,000 and about 20,000.

Poly(maleic acid/methylvinylether) copolymers that can be used preferably have a weight average molecular weight of at least about 50,000, and preferably between about 50,000 and about 4,000,000. The weight average molecular weight is more preferably between about 70,000 and 2,500,000. A general structural representation of poly(maleic acid/methylvinylether) copolymers is shown below:

wherein n is the number of repeating units and is preferably between about 200 and about 20,000.

Additional hydrophilic polymers that can be used include starch, derivatives of starch, polyvinyl alcohol, cellulose, derivatives of cellulose, carboxymethyl cellulose, cyclodextrins, and dextrans. Exemplary starches include amylopectin and polyglucose. The weight average molecular weight of the hydrophilic polymers is preferably sufficient to provide solubility in water but not too high to become difficult to process. Starches that can be used according to the invention preferably have a weight average molecular weight of between about 50,000 and about 20,000,000. A derivative of starch that can be used includes partially hydrolized starch. Cellulose that can be used preferably has a weight average molecular weight of between about 50,000 and about 15,000,000. Polyglucose that can be used can be characterized as low fraction polyglucose having a weight average molecular weight of between about 60,000 and about 90,000, and high fraction polyglucose having a weight average molecular weight of between about 90,000 and about 300,000. An exemplary low fraction polyglucose material that can be used is available under the name Dextran-70. In general, this type of polyglucose has all alpha 1-6 linkages. Starch derivatives that can be used according to the invention include those starch derivatives having alpha 1-4 linkages. An example of this type of starch derivative includes cyclodextrins. Preferred cyclodextrins that can be used are those that act to provide a cavity within the molecule large enough to contain components desirable for applications. Preferably, the cyclodextrins that can be used have a molecular weight of between about 900 and about 1,400. Polyvinyl alcohols that can be used preferably have a weight average molecular weight of between about 50,000 and about 200,000.

Exemplary hydrophilic polymers that can be used include those polymers having the following melting temperature range and the following maximum temperature range beyond which it is expected decomposition of the polymer will occur. Exemplary poly(maleic acid/methylvinylether) copolymers that can be used include those having a melting temperature range of between about 60° C. and about 65° C. and a maximum temperature range of between about 80° C. and about 90° C. Exemplary polyacrylic acid polymers that can be used include those having a melting temperature range of between about 65° C. and about 70° C. and a maximum temperature range of between about 80° C. and about 90° C. Exemplary carboxymethyl cellulose polymers that can be used include those having a melting temperature range of between about 55° C. and about 60° C. and a maximum temperature range of between about 75° C. and about 80° C. Exemplary polyvinyl alcohol polymers that can be used include those having a melting temperature range of between about 50° C. and about 55° C. and a maximum temperature range of between about 65° C. and about 70° C. Exemplary starches that can be used include those having a melting temperature range of between about 40° C. and about 45° C. and a maximum temperature range of between about 50° C. and about 55° C. Exemplary dextrans that can be used include those having a melting temperature range of between about 37° C. and about 40° C. and a maximum temperature range of between about 45° C. and about 50° C. Exemplary β-cyclodextrins that can be used include those having a melting temperature range of between about 40° C. and about 45° C. and a maximum temperature range of between about 65° C. and about 70° C.

Processing

The hydrophobic polymer composition and the hydrophilic polymer composition are preferably combined and mixed as a polymer melt. Preferably, the mixture is heated to at least about 90° C. to provide the polymer melt. Sufficient mixing is introduced to the polymer melt to form a complex between the hydrophobic and hydrophilic polymers. The composition is preferably heated to at least about 100° C., and more preferably at least about 110° C. under mixing to form a complex between the hydrophobic and hydrophilic polymers.

The complex formation step is preferably carried out in a relatively anhydrous environment. That is, the amount of water provided in the composition during the complex formation step is preferably less than about 1 wt. %. Once the desired level of complex formation has occurred, the composition can be hydrated with water.

The hydrophobic polymer composition and the hydrophilic polymer composition are preferably mixed together in amounts sufficient to provide a ratio of pyrrolidone groups to the combination of carboxylic acid groups and hydroxyl groups of between about 1:1 and about 5:1. The ratio of the structures causing the observed interaction between the hydrophobic polymer composition and the hydrophilic polymer composition can be referred to as "functional group parity." Preferably, the ratio of pyrrolidone groups to the combination of carboxylic acid groups and hydroxyl groups is between about 1.5:1 and about 3:1. In order to drive the complex formation reaction, it is desirable to provide an imbalance between the two types of groups. Accordingly, it is generally desirable to provide more of the pyrrolidone groups than the combination of carboxylic groups and the hydroxyl groups. It should be understood that the reference to a "combination of carboxylic groups and hydroxyl groups" refers to the total amount of carboxylic groups and hydroxyl groups present but does not require the presence of both carboxylic groups and hydroxyl groups. For example, the value of the combination of carboxylic groups and hydroxyl groups can be determined for a composition that contains only carboxylic groups. Similarly, the value can be determined for a composition that contains only hydroxyl groups.

During the complex formation step, the amounts of hydrophobic polymer composition and hydrophilic polymer composition can be characterized on a weight percent basis. Preferably, about 2 wt. % to about 28 wt. % hydrophilic polymer composition and about 72 wt. % to about 98 wt. % hydrophobic polymer composition are combined to provide for complex formation. Preferably, about 8 wt. % to about 25 wt. % hydrophilic polymer composition and about 72 wt. % to about 95 wt. % hydrophobic polymer composition are combined to form the complex. During the complex formation step, the amount of water available in the composition is preferably less than about 1 wt. %. Although the complex forming composition can be relatively anhydrous, it is expected that the amount of water will be between about 0.3 wt. % and about 1.0 wt. %.

Once the hydrophobic polymers and the hydrophilic polymers have sufficiently reacted or interacted to form complexes, it is desirable to add water to the composition to provide a stable aqueous composition that can be relatively easily further hydrated. The stable aqueous composition that can be easily diluted further with water to form the use solution can be referred to as the concentrate. It is generally desirable to hydrate the composition to a water content that provides a relatively stable composition and that allows for water to be added at a later date without much difficulty. Although water can be added to the composition to a level equivalent to the level of the composition use solution, it is desirable to minimize the amount of water to avoid having to ship water. Shipping excess water is expected to add cost to the composition. In addition, it has been found that the first hydration of the composition precursor is the most difficult hydration step because of the need to control the conditions of hydration. After the first hydration to a water content of at least about 30 wt. %, it is expected that further hydrations to higher water contents are relatively easy and can be accomplished by simply mixing the composition with water. Accordingly, the amount of water provided in the composition when made available as a concentrate for shipment is preferably between about 30 wt. % and about 45 wt. %. When the composition includes about 30 wt. % to about 45 wt. % water, it is expected that the composition will include between about 3 wt. % and about 10 wt. % hydrophilic polymer composition and between about 30 wt. % and about 50 wt. % hydrophobic polymer composition.

Water is added to the relatively anhydrous composition by mixing water and the relatively anhydrous composition at a temperature and for a time sufficient to allow the composition to become hydrated without losing significant amounts of interaction between the hydrophobic polymer composition and the hydrophilic polymer composition. In general, the relatively anhydrous composition is hydrated by heating to at least 60° C. and adding water while mixing. Preferably, the composition is heated to at least about 65° C. and more preferably at least about 70° C. A preferred temperature range is about 65° C. to about 80° C.

The relatively anhydrous composition can be referred to as the composition concentrate. The composition having a water concentration of between about 30 wt. % and about 95 wt. % can be referred to as the concentrate. The manufacturers of the composition may further hydrate the composition or use it as it is. The transdermal delivery composition can include a sufficient amount of the adduct to hold the cannabinoids in the composition while also releasing the cannabinoids from the composition over a time period of about 4 to 12 hours, preferably about 4 to 6 hours, and also provide a consistent and sustained release. Preferably, the transdermal delivery composition contains about 4 wt. % to about 9 wt. %, more preferably about 4.5 wt. % to about 8 wt. %, and even more preferably about 5 wt. % to about 6 wt. % of the adduct.

For enhancing the release of CBD and THC from the composition, it may be desirable to reduce or lower the hydrophobic character of the polymer complex. This can be done, for example, by providing the polymer complex with about 3 to about 10% polyvinylpyrrolidone hexadecene and about 3 to about 7% of polyvinylpyrrolidone eicosene.

Surfactants

Surfactants can be incorporated into the transdermal delivery composition to provide help solubilize the polymer adduct and to help control the release of active ingredient or other component. It is expected that the amount of surfactant and the type of surfactant can be adjusted as desired. In the case where an active ingredient or other component desired to be released is relatively more hydrophobic, it is expected that by increasing the surfactant concentration, an equilibrium shift favors the aqueous phase and promotes a faster release of the ingredient. Surfactants can be useful for releasing cannabinoids from the transdermal delivery composition because the cannabinoids can be characterized as hydrophobic.

Surfactants that can be incorporated into the composition according to the invention include nonionic surfactants, cationic surfactants, anionic surfactants, and amphoteric surfactants, and mixtures thereof. It may be desirable to use surfactants when they have a tendency to increase the emulsion stability and/or to promote the release of active ingredients. That is, surfactants can be used to increase the water solubility of the polymers of the composition and/or the surfactants can be used to decrease the binding of the cannabinoids to the polymers to thereby enhance release of the cannabinoids.

Nonionic surfactants that can be used include ethoxylated, propoxylated, ethoxylated-propoxylated surfactants, and mixtures thereof. An exemplary nonionic surfactant that can be use includes nonylphenol ethoxylate having nine ethylene oxide groups and is available under the name Nonoxynol-9. Additional exemplary nonionic surfactants that can be used include Poloxamer surfactants such as Poloxamer 124 and Poloxamer 237, and are available under the trade names Synperonics, Pluronics, and Kolliphor.

Anionic surfactants that can be used include carboxylic salts (soaps) and sulfonate salts (detergents). Cationic surfactants that can be used include amides such as cocoamide. One concern with the use of anionic surfactants, cationic surfactants, and amphoteric surfactants relates to the potential destabilization of emulsions as a result of the presence of salts. Accordingly, it may be desirable to use anionic surfactants, cationic surfactants, and amphoteric surfactants at sufficiently low levels to reduce this destabilizing effect. It is expected that these surfactants will be used at lower levels than nonionic surfactants. In addition, the positive charge of the cationic surfactants and the amphoteric surfactants can have an effect of forming insoluble complexes with portions of the hydrophilic polymer composition.

Addition of surfactant can assist in release of CBD and THC from the composition. In an example, the release of CBD and THC of 4.3% and 3% respectively, and at a ratio of 0.7, increased to 30.2% and 21.7% respectively, and at a ratio of 0.72.

When surfactants are used, it is generally desirable to use the surfactant or mixture of surfactants in an amount that provides a desired level of emulsion stability and provides a desired rate of release of cannabinoids. It is expected that in most applications, the surfactant or mixture of surfactants will be provided at a concentration of about 3 wt. % to about 9 wt. %, preferably about 3.5 wt. % to about 8 wt. %, and more preferably about 4 wt. % to about 6 wt. %.

Skin Penetrants

Skin penetrants can be referred to as skin penetrators, penetrant components, or penentrants, and can be incorporated into the transdermal delivery composition to enhance penetration of the cannabinoids through the skin tissue. Once the CBD and THC have been released from the composition, the penetrant helps the CBD and THC enter through the skin tissue. Exemplary skin penetrants that can be used include caprylic acid, capric acid, lauric acid, myristic acid, palmitic acid, linoleic acid, linolenic acid, oleic acid, elaidic acid, 10-methyl palmitic acid, 10-methyl hexadec-9-enoic acid, 7-methyl octanoic acid, 9-methyl decanoic acid, 8-ethyl decanoic acid, 10-ethyl dodecanoic acid, lauryl choline, terpenes, anethole, α-bisabolol, sesquiterpene, borneol, camphor, carvacrol, carvone, 1,8-cineole, cymene, 1,4-cineole, cymene, eugenol, linalool, menthol, menthone, menthol menthone, farnesol, geraniol, limonene, nerolidol, α-pinene, neorxoildideol, α-pinene oxide, α-pinene oxide pulegone, terpinen-4-ol (4-te(r4p-tienrepninoeln)ol), tetra-hydrogeraniol, thymol valen-cene, verbenon-e, and mixtures thereof. Preferred skin penetrants include a mixture of oleic acid and terpene.

The transdermal delivery composition can include a penetrant in an amount sufficient to enhance the transdermal delivery of the cannabinoids. Preferably, the transdermal delivery composition contains at least about 1 wt. % penetrant, more preferably about 2 wt. % to about 10 wt. % penetrant, more preferably about 3 wt. % to about 7 wt. % penetrant, and more preferably about 3.5 wt. % to about 5 wt. % penetrant.

Antioxidants

The transdermal delivery composition can include antioxidants to help reduce decomposition of the cannabinoids. Exemplary antioxidants that can be used include (3-carotene, lycopene, lutein, glutathione, melatonin, oestrogen, ubiquinol-10, N-acetyl cysteine, lipoic acid(LA), zinc, selenium, copper, quercetin, catechin, cortisone, estradiol, estriol, α-tocopherol, ascorbic acid, butylatedhydroxytoluene (BHT), butylatedhydroxyanisole(BHA), 2,3-dimercaptosuccinic acid (DMSA), monoisoamyldimercaptosuccinic acid, dihydrolipoic acid (DHLA), gallic acid, propygallate, α-tocopherolacetate, vitamin E, vitamin E acetate, synthetic forms of vitamin E, and mixtures thereof. The antioxidant is an optional component, but when the transdermal delivery composition contains an antioxidant, it can include less than about 0.03 wt. % antioxidant, preferably about 0.1 wt. to about 1 wt. % antioxidant, and more preferably about 0.2 wt. % to about 0.5 wt. % antioxidant.

Chelating Agents

The transdermal delivery composition can include a chelating agent to react with metal ions in the water of the composition to form a stable, water-soluable complex. Various exemplary chelating agents are well known. A preferred chelating agent can be used includes ethylenediamientetraacetic acid (EDTA). The presence of a chelating agent in the composition is optional and typically depends on the quality of the water used to form the composition. When included in the transdermal delivery composition, the chelating agent is preferably provided in an amount sufficient to provide chelating properties. Exemplary ranges of chelating agent that can be included in the transdermal delivery composition includes less than about 0.05 wt. %, and more preferably 0.01 wt. % to about 0.1 wt. %.

Emollients

The transdermal delivery composition can include an emollient to provide a desirable feel to the composition. Exemplary emollients that can be used include mineral oil, lanolin oil, coconut oil, cocoa butter, olive oil, almond oil, macadamia nut oil, synthetic jojoba oils, natural sonora jojoba oils, safflower oil, corn oil, aloe vera, cottonseed oil, peanut oil, squalene, castor oil, polybutene, odorless mineral spirits, sweet almond oil, avocado oil, clophyllum oil, ricin oil, vitamin E acetate, linolenic alcohol, oleyl alcohol, cereal germ oils, wheat germ oil, isopropyl palmitate, isopropyl myristate, hexadecyl stearate, butyl stearate, decyl oleate, acetyl glycerides, octanoates and benzoates of ($C_{12}$-$C_{15}$) alcohols, octanoates and decanoates of alcohols and polyalcohols glycol and glycerol, isopropyl adipate, hexyl laurate, octyl dodecanoate, hydrogenated lanolin, hydroxylated lanolin, acetylated lanolin, petrolatum, isopropyl lanolate, butyl myristate, cetyl myristate, myristyl myrislate, myristyl lactate, cetyl alcohol, isostearyl alcohol, isocetyl lanolate, stearic acid, stearyl alcohol, palmitic acid esters, natural and synthetic esters such as coconut oil, and mixtures thereof.

The presence of an emollient in the composition is optional, but when it is present, it is preferably present in an amount of about 1 wt. % to about 5 wt. %, and more preferably about 1.5 wt. % to about 4 wt. %.

Water

The transdermal delivery composition can include an amount of water so that the composition can be applied conveniently to the skin tissue. Preferably, the transdermal delivery composition includes water in an amount of about 70 wt. % to about 90 wt. %, and preferably about 75 wt. % to about 85 wt. %.

pH Neutralizing Agent

The transdermal delivery composition is preferably provided at a pH sufficient for the delivery and penetration of the cannabinoid mixture. The composition can include a pH neutralizing agent to provide the composition with a pH in the range of about 6 to about 7.5. Known pH neutralizing agents can be used including, for example, triethanolamine (TEA).

Additional Components

The transdermal delivery composition is preferably prepared by mixing the components for the formation of the transdermal delivery composition. Components that can be incorporated into the composition for forming the use solution include those components normally encountered in the topical composition industry. Exemplary components include preservatives such as antimicrobial agents. The presence of a preservative in the composition is optional, but when it is present, it is preferably present in an amount of about 0.1 wt. % to about 2 wt. %, and more preferably about 0.5 wt. % to about 1.5 wt. %.

Application

The transdermal delivery composition can be applied to skin tissue in an amount that provides a desired effect. For example, the composition can be applied in a volumetric amount equal to about two dimes to a quarter (United States currency) to clean, dry skin. Preferably to the solar forearm or an area of concern, spread to an even film, and allowed to dry. The effects can generally be felt or noticed within about 15 to 20 minutes. The composition can be re-applied, as desired.

EXAMPLES

The following examples were carried out to demonstrate advantages of the present disclosure. It should be understood that the invention is not limited to the examples of this application.

Example 1

This example is modeled on providing a 1:1 weight ratio of Cannabidiol (CBD) to $\Delta^9$-Tetrahydrocannabinol (THC) for therapeutic effect based on an article by Dr. Malik Burnett (https://www.medicaljane.com/2014/05/29/finding-the-optimal-therapeutic-ratio-of-thc-and-cbd/). A transdermal product delivering a 1:1 ratio of CBD to THC is believed to provide enhanced therapeutic efficacy. Indeed, based on another article (http://mychronicrelief.com/cannabis-science/cannabinoids/), it appears that CBD and THC together have a greater therapeutic effect than either one alone.

CBD and THC are similar in structure and sparingly soluble in aqueous buffers. They are readily soluble in organic solvents, complicating the delivery process since skin poorly tolerates organic solvents. The polymers used in this example to hold and release the cannabinoids are very hydrophobic, containing an abundance of polyvinylpyrrolidone polymers with C16, C20, and in some cases C30 side chains (U.S. Pat. Nos. 8,318,818 and 8,481,058). CBD and THC are readily soluble in these polymer complexes.

This hydrophobic property of the polymer delivery system complicates the transdermal process as transdermal delivery through the skin is a two-step process. First, the active ingredient(s) must be released from the vehicle, in this case the polymers. If the active remains in the vehicle, it will have no therapeutic effect. Second, the active ingredient(s) must penetrate the skin, an organ whose nature is to resist such a process.

Active ingredient release from the vehicle can be accomplished in two ways. The first method is by the use of surfactants. The judicious choice of surfactants, can increase the partition of the active ingredient between the polymer phase and the aqueous phase, thus enhancing the release of the active. The second method is to decrease the hydrophobic character of the polymer composition. Due to the highly flexible nature of the polymer complex, this is relatively easy to do. The polymer composition used to form the complex or adduct includes about 5% to about 15%, and preferably about 7% to about 12%, polyvinylpyrrolidone/hexadecene, and about 1% to about 7%, and preferably about 3% to about 6%, polyvinylpyrrolidone/eicosene. In addition, the transdermal delivery composition includes this polymer complex and a mixture of surfactants to help release the CBD and THC.

The molecular weight of the active is relevant to the ability of the active to penetrate the skin. A molecular weight of less than 600 to 1000 is considered to have the best chance of penetrating through the skin. CBD and THC both have a molecular weight of 314.22, well below the exclusion limit for the skin. It is best that the active have no charge and is relatively hydrophobic. Skin penetrants are included to yield a reasonably high level of skin penetration by CBD and THC as measured with Franz Cells.

Figure 1:
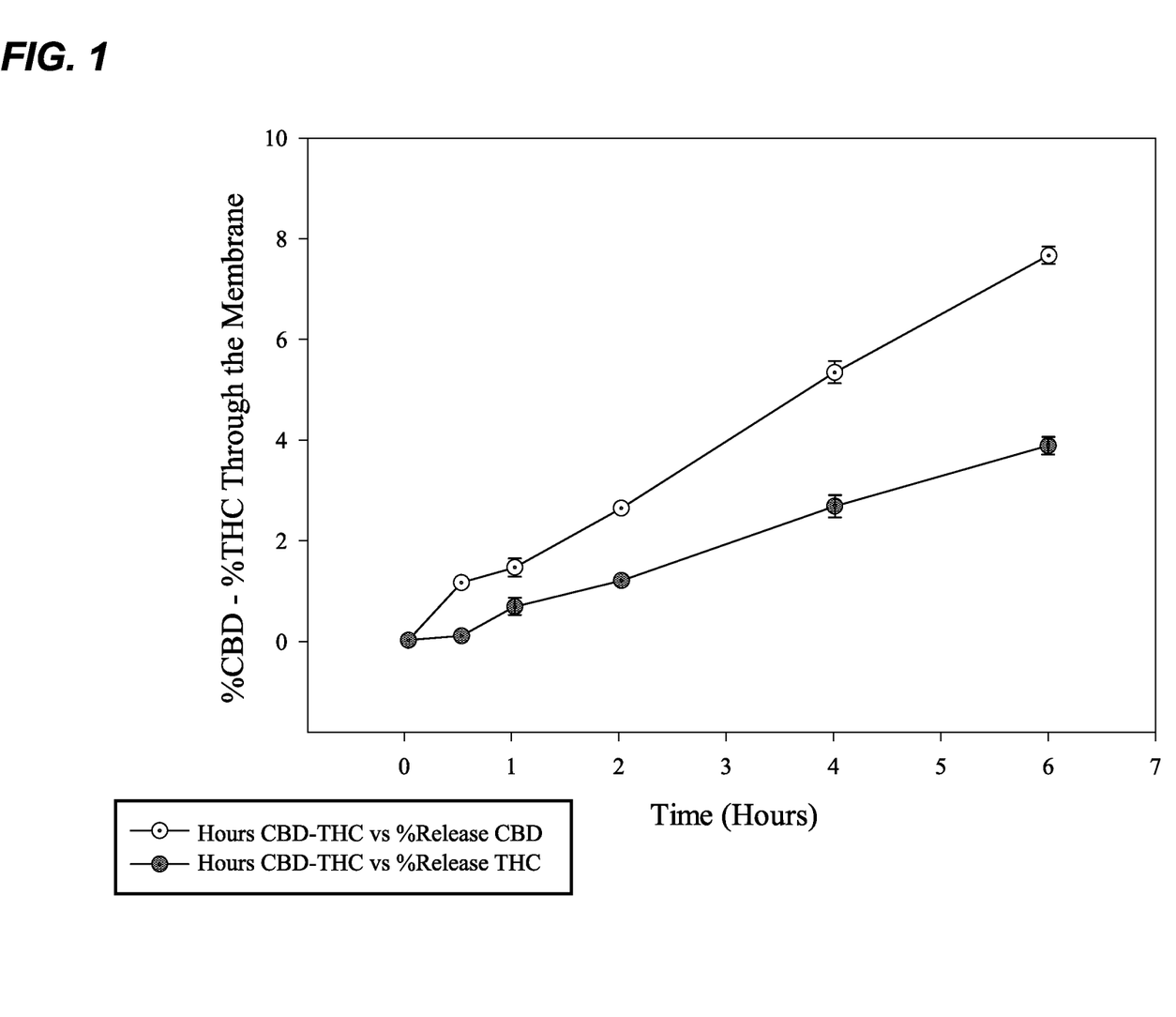
FIG. 1 is a graph showing the percent of CBD or THC released as a function of time according to Example 1.

A six-hour Franz Cell study using the above formulation yielded the results reported in FIG. 1.

The penetration of CBD is consistently higher than the penetration of THC, which is a reflection of the release data. The penetration of CBD is nearly 4 times higher than the THC at 6 hours.

The seemingly simplest way to achieve a release ratio of 1:1 is to increase the penetrant, thereby increasing the release of both actives, and the subsequent penetration of the skin. Initially, the amount of penetrant was increased from 1% to 3%. The penetration of CBD decreased to 5.8% and the THC dropped to 3.2%. This was an unexpected result and the results were not shifting in the desired direction.

Example 2

Figure 2:
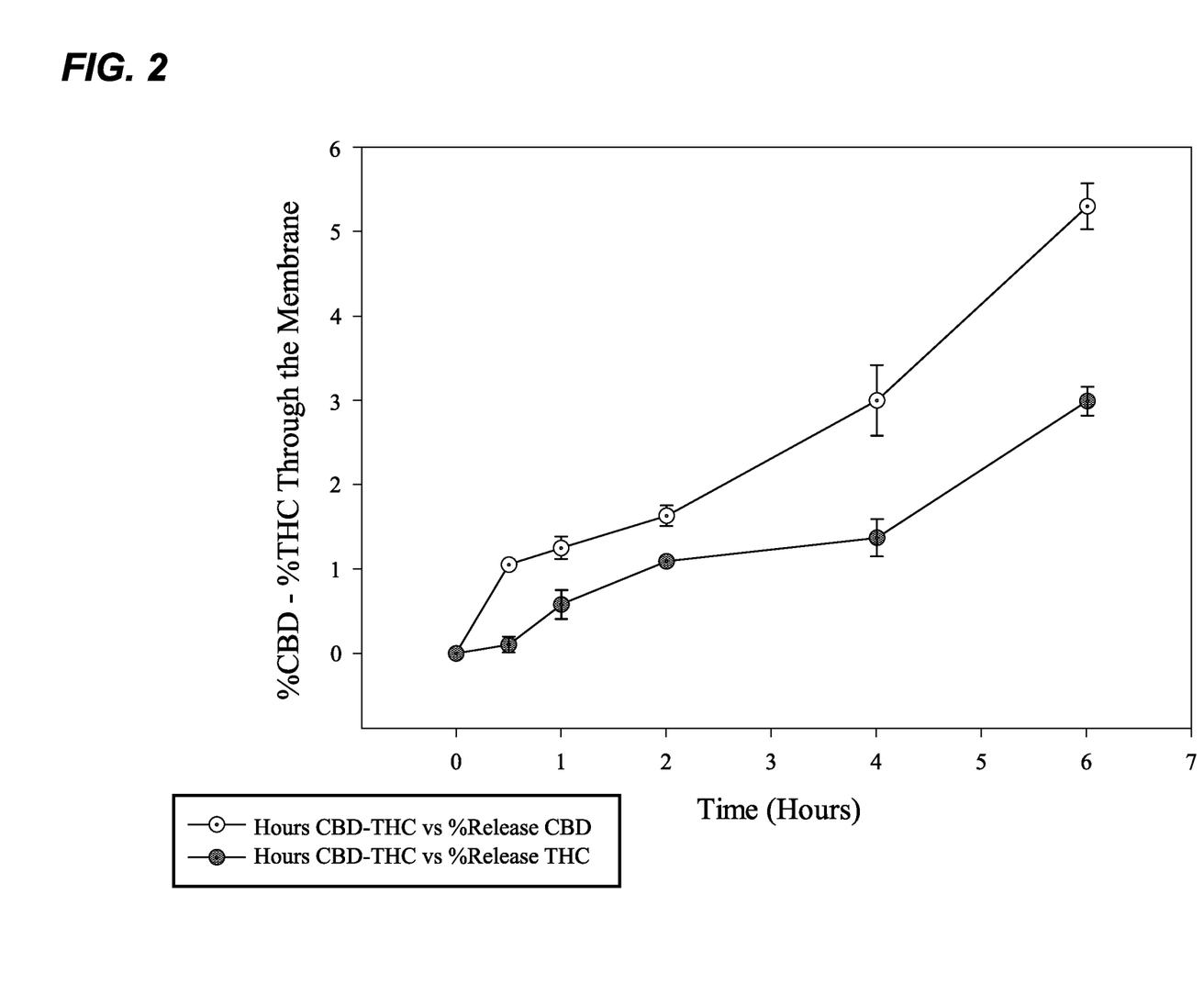
FIG. 2 is a graph showing the percent of CBD or THC released as a function of time according to Example 2.

Another attempt to lower the amount of CBD with respect to the THC was to decrease the amount of CBD in the formulation. A Franz cell study of a ratio of 1:2 CBD:THC (0.34%:0.68%) is shown in FIG. 2. The composition was otherwise the same as the composition of example 1.

Although the CBD release decreased to only twice that of the THC it still did not achieve the desired 1:1 ratio of CBD:THC.

Example 3

Figure 3:
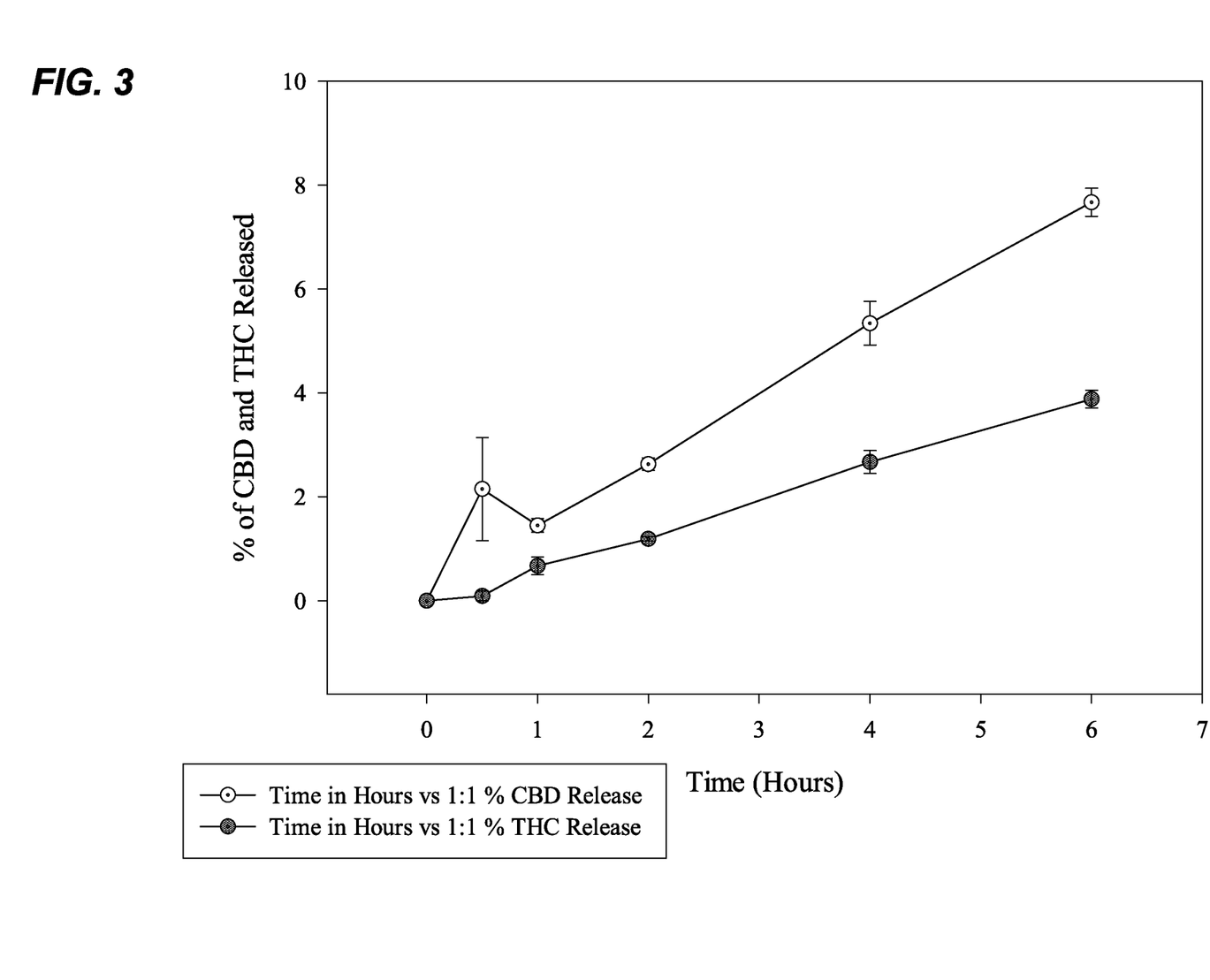
FIG. 3 is a graph showing the percent of CBD and THC released as a function of time according to Example 3.

A six-hour Franz Cell study using the above formulation and a weight ratio of 1:1 CBD:THC yielded the results depicted in FIG. 3.

The penetration of CBD is consistently higher than the penetration of THC, which is a reflection of the release data presented in FIG. 3. The penetration of CBD is nearly 2 times higher than the penetration of THC at 6 hours. The actual weight ratio of CBD:THC is 1.98.

Although the formulated weight ratio of CBD to THC in the composition is 1:1, the resulting penetration data is more like 2:1. This disparity between the formulated amount and penetration amount is possibly due to the differences in release between CBD and THC as previously noted above although the ratio of 0.7 is not preserved. An attempt to decrease the ratio of CBD to THC involved increasing the amount of terpene penetrant to increase the release of both CBD and THC, and the subsequent penetration of the skin tissue. Initially, the terpene was increased from 1% to 3%. As a result, the penetration of CBD decreased to 5.8% and the THC dropped to 3.2%. This was an unexpected result in that an increase in penetrant resulted in a decrease in both CBD and THC penetration.

Example 4

Figure 4:
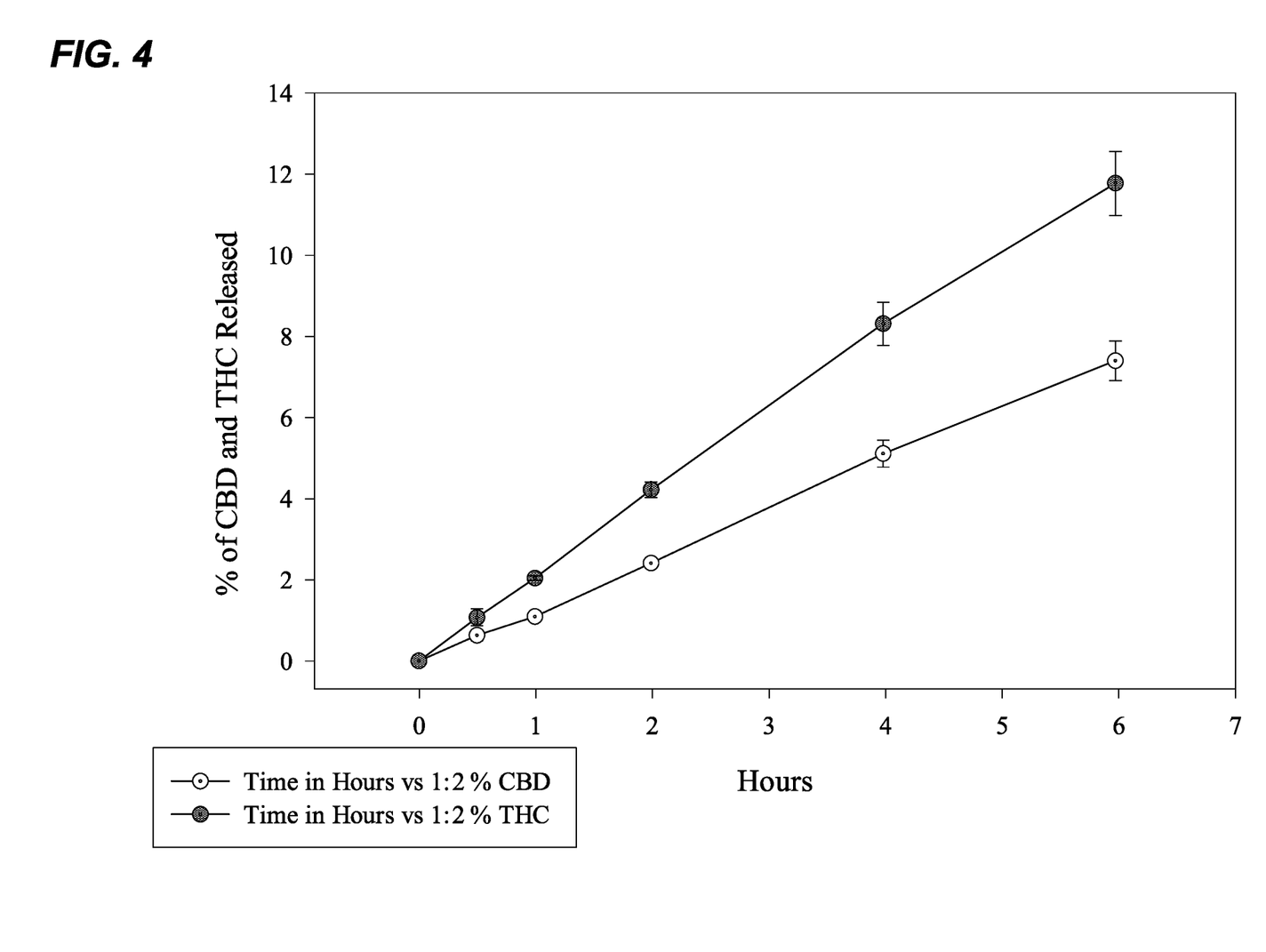
FIG. 4 is a graph showing percent of CBD and THC released as a function of time according to Example 4.
Figure 5:
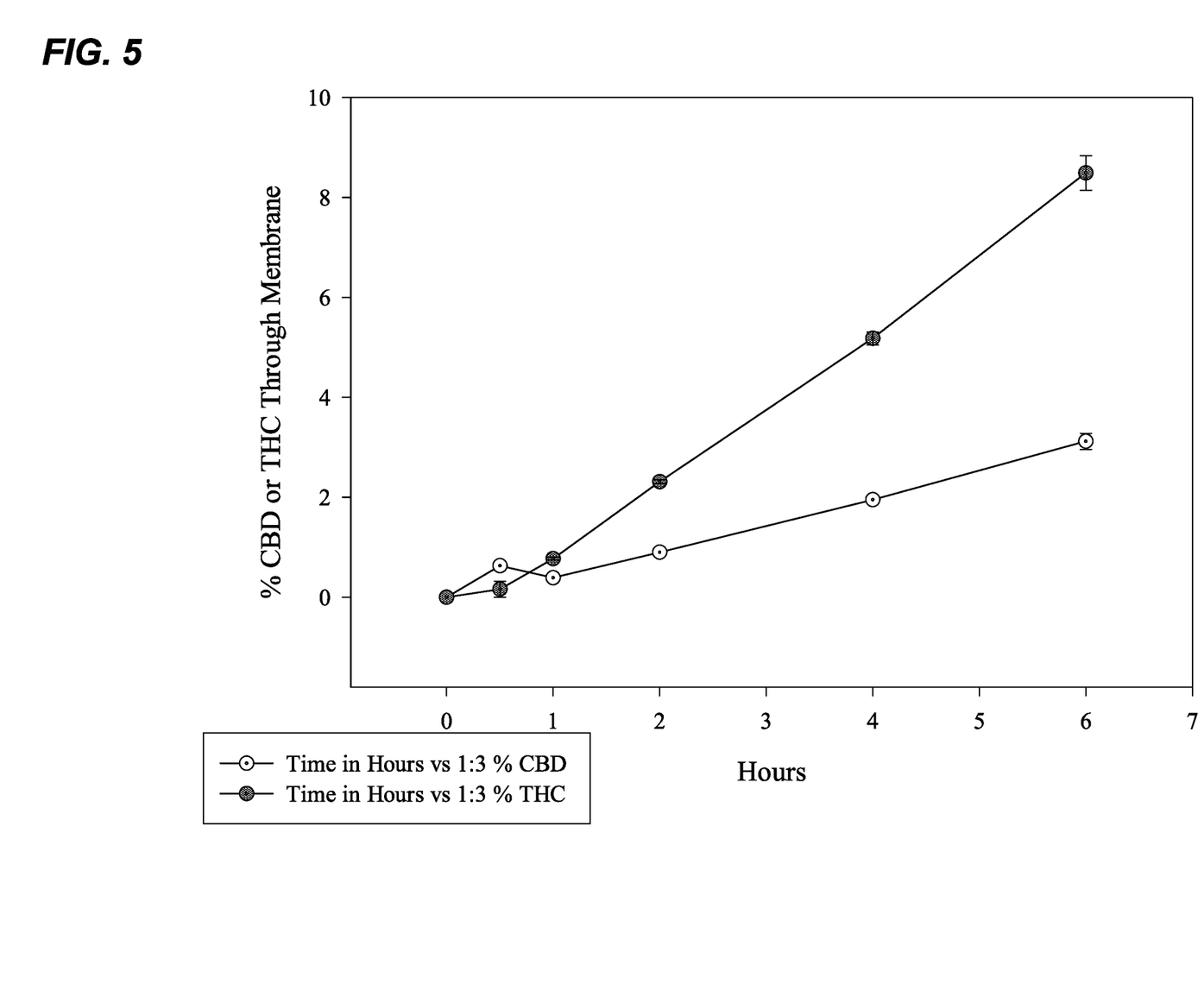
FIG. 5 is a graph showing the percent of CBD or THC passing through a membrane as a function of time according to Example 4.
Figure 6:
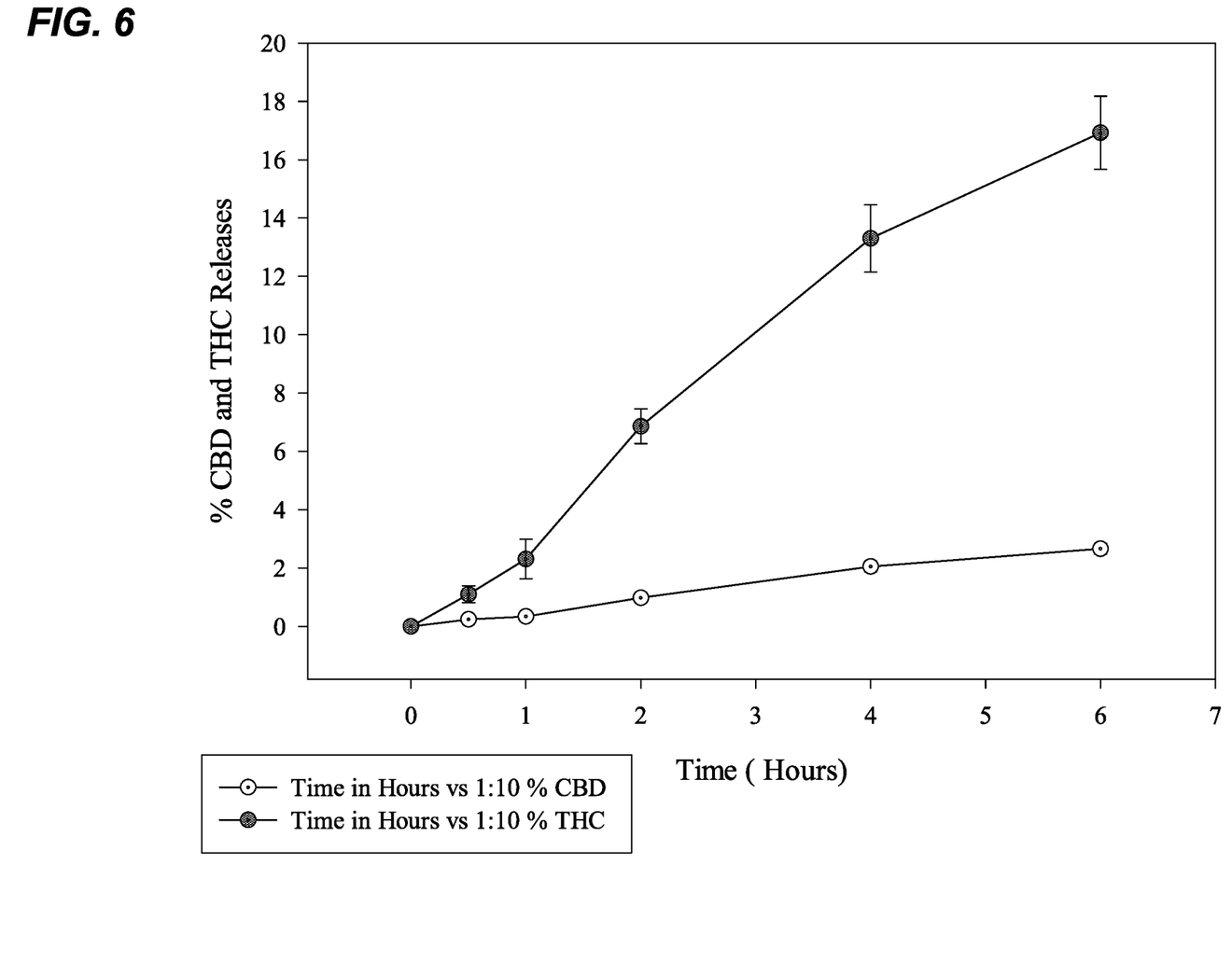
FIG. 6 is a graph showing the percent of CBD and THC released as a function of time according to Example 4.

Another attempt to lower the penetration of CBD relative to THC involved decreasing the amount of CBD in the formulation. A Franz cell study of a ratio of 1:2 CBD:THC is shown in FIG. 4, a Franz cell study of a ratio of 1:3 CBD:TCC is shown in FIG. 5, and a Franz cell study of a ratio of 1:10 CBD:TCC is shown in FIG. 6. The results shown in FIGS. 4 and 5 shows a penetration approaching 1:1 as the formulation ratio diverges from 1:1. FIG. 6 shows a penetration ratio approaching the formulation ratio.

Although the relationship between formulated CBD:THC ratios and the delivered ratios (penetration ratio) is not likely due to the relative solubilities of CBD and THC in the polymers, polymer/surfactant mixture, or the solubilities in the phosphate buffered saline of the receiving chamber of the Franz cells. For therapeutic purposes, this example was directed at learning how to predict a delivered CBD:THC ratio from a formulated CBD:THC ratio.

Figure 7:
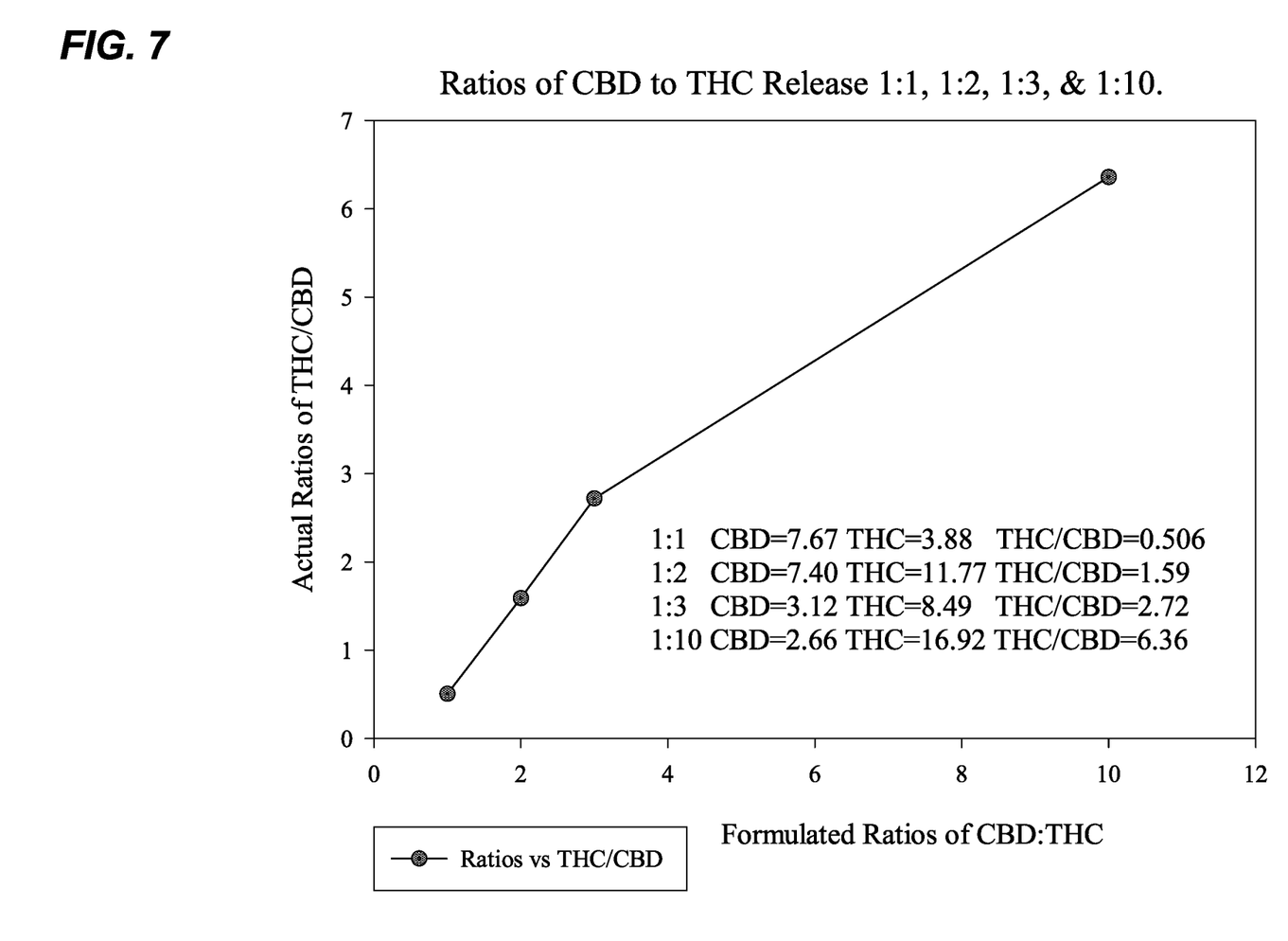
FIG. 7 is a graph showing actual ratios of THC/CBD as a function of formulated ratios of CBD:THC according to Example 4.

A partial method for the solution of this issue is illustrated in FIG. 7. FIG. 7 includes the formulation ratios of CBD:THC versus actual, delivered ratios of CBD:THC. The portion of the curve between 1:1 and 1:3 is linear and may be used to predict a desired CBD:THC ratio from a formulated ratio. For example, if a 1:1 delivered ratio is desired one would formulate at ~1:1.5 based on FIG. 7. This ratio can be referred to as a CBD/THC delivery factor, and it can be used to determine the formulation ratio of CBD to THC to be used when formulating the transdermal delivery composition. The linear portion of the curve may extend beyond the 1:3 ratio, but it is not yet clear how long this linear relationship will continue. This relationship, however, can be used to predict a desired delivery ratio of CBD:THC based on a formulated ratio.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A transdermal delivery composition comprising:
    (a) at least 0.05 wt. % of a cannabinoid mixture, wherein the cannabinoid mixture comprises cannabidiol (CBD) and $\Delta^9$-tetrahydrocannabinol (THC) at a weight ratio of about 20:1 to about 1:20;
    (b) a hydrophilic polymer/hydrophobic polymer adduct in an amount sufficient to hold the cannabinoid mixture and provide a sustained release of the cannabinoid mixture after application to skin tissue, wherein the hydrophobic polymer/hydrophilic polymer adduct comprises at least two different poly(vinylpyrrolidone/alkylene) polymers, wherein the alkylene group of each polymer contains at least 10 carbon atoms, and wherein the hydrophilic polymer/hydrophobic polymer adduct comprises poly(maleic acid/methylvinylether) copolymer having a weight average molecular weight of about 50,000 to 4,000,000;
    (c) 3.5 wt. % to 5 wt. % of penetrant component comprising a mixture of oleic acid and limonene to assist with a transdermal penetration of the cannabinoid mixture through skin tissue once the composition has been applied to skin tissue;

(d) about 3 wt. % to about 9 wt. % of a surfactant component to release the cannabinoid mixture from the transdermal delivery composition upon application to skin tissue; and (e) at least about 70 wt. % water.

2. A transdermal delivery composition according to claim 1, wherein the at least two different poly(vinylpyrrolidone/alkylene) polymers comprise poly(vinylpyrrolidone/1-eicosene) and poly(vinylpyrrolidone/hexadecene).

3. A transdermal delivery composition according to claim 1, wherein the cannabinoid mixture comprises the CBD and THC at a weight ratio of about 10:1 to about 1:10.

4. A transdermal delivery composition according to claim 1, wherein the composition further comprises an emollient in an amount of about 1 wt. % to about 5 wt. %.

5. A transdermal delivery composition according to claim 1, wherein the composition further comprises an antioxidant in an amount of about 0.1 wt. % to about 1 wt. %.

6. A transdermal delivery composition according to claim 1, wherein the composition further comprises a pH neutralizing agent in an amount sufficient to provide a pH of about 6-7.5.

7. A transdermal delivery composition according to claim 1, wherein the transdermal delivery composition provides a sustained release of the cannabinoid mixture after application to skin tissue over a time period of at least 4 hours.

8. A transdermal delivery composition according to claim 1, wherein the transdermal delivery composition provides a sustained release of the cannabinoid mixture after application to skin tissue over a time period of at least 6 hours.

9. A transdermal delivery composition according to claim 1, wherein the transdermal delivery composition comprises 0.05 wt. % to 2 wt. % of the cannabinoid mixture.

10. A transdermal delivery composition according to claim 1, wherein the transdermal delivery composition comprises 0.1 wt. % to 1.5 wt. % of the cannabinoid mixture.

* * * * *